(12) United States Patent
Webster et al.

(10) Patent No.: US 7,399,872 B2
(45) Date of Patent: Jul. 15, 2008

(54) CONVERSION OF CBD TO Δ⁸-THC AND Δ⁹-THC

(76) Inventors: G. R. Barrie Webster, 71 Wildwood Park, Winnipeg, Manitoba (CA) R3T 0C8; Leonard P. Sarna, 37 Arena Road, Ste. Anne, Manitoba (CA) R4H 1H8; Raphael Mechoulam, Hebrew University Medical Faculty, Ein Kerem Campus, 91120 Jerusalem (IL)

( * ) Notice: Subject to any disclaimer, the term of this patent is extended or adjusted under 35 U.S.C. 154(b) by 151 days.

(21) Appl. No.: 10/469,928

(22) PCT Filed: Mar. 7, 2002

(86) PCT No.: PCT/CA02/00451

§ 371 (c)(1),
(2), (4) Date: Feb. 25, 2004

(87) PCT Pub. No.: WO02/070506

PCT Pub. Date: Sep. 12, 2002

(65) Prior Publication Data

US 2004/0143126 A1    Jul. 22, 2004

Related U.S. Application Data

(60) Provisional application No. 60/273,628, filed on Mar. 7, 2001.

(51) Int. Cl.
*C07D 311/80*    (2006.01)

(52) U.S. Cl. .................................................... 549/390
(58) Field of Classification Search ................ 549/390
See application file for complete search history.

(56) References Cited

U.S. PATENT DOCUMENTS 4,116,979 A    9/1978    Dalzell et al.
5,342,971 A    8/1994    Herlt et al.

OTHER PUBLICATIONS

Gaoni, Yehiel et al, "Hashish-VII: The isomerization of Cannabinol to Tetrahydrocannabinols", *Tetrahedron*, vol. 22, 1966, pp. 1481-1488.
Gaoni, Yehiel et al, "The isolation and structure of Delta-1-Tetrahydrocannabinol and other neutral Cannabinoids from Hashish", *J. Am. Chem. Soc.*; vol. 93, No. 1, 1971, pp. 217-224.
Adams, Roger et al, "Structure of Cannabidiol. XII. Isomerization to Tetrahydrocannabinols", *J. Am. Chem. Soc.*, vol. 63, 1941, pp. 2209-2213.
Volicer, Ladislav et al, "Effects of Dronabinol on Anorexia and disturbed behavior in patients with Alzheimer's disease", *International Journal of Geriatric Psychiatry*, John Wiley and Sons, Chichester, GB; vol. 12, No. 9, Sep. 1997, pp. 913-919.
Marijuana and Medicine Assessing the Science Base; Janet E. Joy, Stanley J. Watson, Jr., and John A. Benson; Division of Neuroscience and Behavioral Health, Institute of Medicine; pp. 137 to 191.

*Primary Examiner*—Rei-tsang Shiao
(74) *Attorney, Agent, or Firm*—Michael R. Williams; Adrian D. Battison; Ryan W. Dupuis

(57) ABSTRACT

Methods of converting cannabidiol to Δ⁸-tetrahydrocannabinol or Δ⁹-tetrahydrocannabinol are described. The described methods produce higher yields and higher purity compared to prior art methods.

7 Claims, No Drawings

CONVERSION OF CBD TO $\Delta^8$-THC AND $\Delta^9$-THC

This application claims priority under 35 USC 119(e) to Provisional Patent Application Ser. No. 60/273,628, filed Mar. 7, 2001.

FIELD OF THE INVENTION

The present invention relates generally to the field of chemical synthesis. More specifically, the present invention relates methods of converting CBD to $\Delta^8$-THC or $\Delta^9$-THC.

BACKGROUND OF THE INVENTION

Recently, public interest in *Cannabis* as medicine has been growing, based in no small part on the fact that *Cannabis* has long been considered to have medicinal properties, ranging from treatment of cramps, migraines, convulsions, appetite stimulation and attenuation of nausea and vomiting. In fact, a report issued by the National Academy of Sciences' Institute of Medicine indicated that the active components of *Cannabis* appear to be useful in treating pain, nausea, AIDS-related weight loss or "wasting", muscle spasms in multiple sclerosis as well as other problems. Advocates of medical marijuana argue that it is also useful for glaucoma, Parkinson's disease, Huntington's disease, migraines, epilepsy and Alzheimer's disease.

Marijuana refers to varieties of *Cannabis* having a high content of $\Delta^9$-tetrahydrocannabinol ($\Delta^9$-THC), which is the psychoactive ingredient of marijuana whereas industrial hemp refers to varieties of the *Cannabis* plant that have a low content of $\Delta^9$-THC.

Furthermore, $\Delta^9$-THC is only one of a family of about 60 bi- and tri-cyclic compounds named cannabinoids. For example, $\Delta^8$-THC is a double bond isomer of $\Delta^9$-THC and is a minor constituent of most varieties of *Cannabis* (Hollister and Gillespie, 1972, *Clin Pharmacol Ther* 14: 353). The major chemical difference between the two compounds is that $\Delta^9$-THC is easily oxidized to cannabinol whereas $\Delta^8$-THC does not and is in fact very stable. $\Delta^8$-THC, for the most part, produces similar psychometric effects as does $\Delta^9$-THC, but is generally considered to be 50% less potent than $\Delta^9$-THC and has been shown in some cases to be 3-10 times less potent. $\Delta^8$-THC has also been shown to be more (200%) effective an anti-emetic than $\Delta^9$-THC and has been used as an anti-emetic in children, based on the belief that the side effects of $\Delta^9$-THC and $\Delta^8$-THC, such as anxiety and dysphoria, are more prevalent in adults than children (Abrahamov et al, 1995, *Life Sciences* 56: 2097-2102). On the other hand, CBD has no activity on its own when administered to humans. It is of note that CBD is typically about 2% (0.5-4%) dry weight of hemp chaff, $\Delta^8$-THC is approximately 0.2% (0.05-0.5%) dry weight and $\Delta^9$-THC is approximately 0.1% (0.05-0.3%).

Gaoni and Mechoulam (1966, *Tetrahedron* 22: 1481-1488) teach methods of converting CBD to, among other compounds, $\Delta^8$-THC and $\Delta^9$-THC comprising boiling a solution of CBD (3.0 g) in absolute ethanol (100 ml) containing 0.05% HCl for 18 hours. The solution was then poured into water and extracted with ether. The ether solution was washed with water, dried ($Na_2SO_4$) and evaporated. $\Delta^8$-THC and $\Delta^9$-THC were eluted from the resulting oil and separated by chromatography. In another experiment, CBD (3.14 g) was dissolved in benzene (100 ml) containing 2 mg/ml p-toluenesulphonic acid and boiled for two hours. The reaction mixture was poured into water and the upper layer was separated, washed with 5% $NaHCO_3$, then with water, dried and evaporated. Elution with pentane-ether (95:5) gave an oily material which was subsequently distilled. Percentage yield of $\Delta^8$-THC ($\Delta^{1(6)}$-THC) was given as 64% of the crude material in this paper. The crude oil product, which showed only one spot by thin layer chromatography, was purified by vacuum distillation.

Gaoni and Mechoulam (1964, *J Amer Chem Soc* 86: 1646) also described a method for converting CBD to $\Delta^9$-THC comprising boiling a mixture of CBD in ethanol containing 0.05% hydrogen chloride for 2 hours. Percentage yield of $\Delta^9$-THC ($\Delta^1$-THC) was 2% (Mechoulam et al, 1972, *J Amer Chem Soc* 94: 6159-6165; Mechoulam and Gaoni, 1965, *J Amer Chem Soc* 87: 3273). Using boron trifluoride, the yield was 70% (Gaoni and Mechoulam, 1971, *J Amer Chem Soc* 93: 217-224) although purity was not given.

Clearly, as the cannabinoids are of potential medicinal value, improved methods of converting CBD to $\Delta^9$-THC or $\Delta^8$-THC are needed.

SUMMARY OF THE INVENTION

According to a first aspect of the invention, there is provided a method of converting CBD to a tetrahydrocannabinol comprising:
providing a reaction mixture comprising a catalyst in an organic solvent;
adding CBD to the reaction mixture;
mixing said reaction mixture;
allowing the mixture to separate into an aqueous phase and an organic phase;
removing the organic phase; and
eluting the tetrahydrocannabinol from the organic phase.

According to a second aspect of the invention, there is provided a method of converting CBD to $\Delta^8$-THC comprising:
providing a reaction mixture comprising a Lewis acid in an organic solvent;
adding CBD to the reaction mixture;
refluxing said reaction mixture under a nitrogen atmosphere;
diluting the mixture with an organic solvent;
pouring the mixture into cold water;
mixing the mixture;
allowing the mixture to separate into an aqueous phase and an organic phase;
removing the organic phase; and
eluting $\Delta^8$-THC from the organic phase.

According to a third aspect of the invention, there is provided a method of converting CBD to $\Delta^9$-THC comprising:
providing a reaction mixture comprising CBD in an organic solvent;
adding a catalyst to the reaction mixture under a nitrogen atmosphere;
stirring the reaction mixture;
adding $NaHCO_3$ to the reaction mixture;
allowing the mixture to separate into an aqueous phase and an organic phase;
removing the organic phase; and
eluting $\Delta^9$-THC from the organic phase.

According to a fourth aspect of the invention, there is provided a method of preparing a pharmaceutical composition comprising:
converting CBD to a tetrahydrocannabinol by:
providing a reaction mixture comprising a catalyst in an organic solvent;
adding CBD to the reaction mixture;
mixing said reaction mixture;

allowing the mixture to separate into an aqueous phase and an organic phase;
removing the organic phase; and
eluting the tetrahydrocannabinol from the organic phase; and
mixing the eluted tetrahydrocannabinol with a suitable excipient.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, CBD refers to cannabidiol.

As used herein, $\Delta^9$-THC refers to $\Delta^9$-tetrahydrocannabinol.

As used herein, $\Delta^8$-THC refers to $\Delta^8$-tetrahydrocannabinol.

As used herein, "Lewis acid" refers to a powerful electron pair acceptor. Examples include but are by no means limited to $BF_3Et_2O$, p-toluenesulfonic acid and boron trifluoride.

Described herein are methods and protocols for converting cannabidiol (CBD) to $\Delta^8$-tetrahydrocannabinol ($\Delta^8$-THC) or $\Delta^9$-tetrahydrocannabinol ($\Delta^9$-THC). As will be appreciated by one knowledgeable in the art and as discussed below, the reaction times may be varied somewhat, producing product at different yields and purities. Furthermore, functional equivalents may be substituted where appropriate.

Specifically, described herein is a method of converting CBD to a tetrahydrocannabinol comprising: providing a reaction mixture comprising a catalyst in an organic solvent, adding CBD to the reaction mixture, mixing said reaction mixture, allowing the mixture to separate into an aqueous phase and an organic phase; removing the organic phase, and eluting the tetrahydrocannabinol from the organic phase. The tetrahydrocannabinol may then be combined with suitable excipients known in the art, thereby forming a pharmaceutical composition.

In some embodiments, the tetrahydrocannabinol at therapeutically effective concentrations or dosages be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly (lactic acid), gelatin, collagen matrices, polysaccharides, poly(D,L lactide), poly(malic acid), poly(caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, *Remington: The Science and Practice of Pharmacy*, 1995, Gennaro ed.

In some embodiments, the catalyst is a Lewis acid, for example, p-toluenesulfonic acid, boron trifluoride or $BF_3Et_2O$. In some embodiments, the $BF_3Et_2O$ is in dry methylene chloride, ehtyl acetate, ethanol, hexane or other organic solvent. In yet other examples, the catalyst may be hydrochloric acid in ethanol or sulfuric acid in cyclohexane.

In some embodiments, a weak base is added to the reaction mixture prior to allowing the reaction mixture to separate into organic and aqueous phases. The base may be an alkali metal hydrogen carbonate or a carbonate of an alkali metal.

In some embodiments, the organic layer is dried prior to eluting. In these embodiments, a suitable drying or dehydration compound, for example, $MgSO_4$ or $Na_2SO_4$ is used.

In yet other embodiments, the process may be carried out under a nitrogen atmosphere.

As discussed below, yield is determined by looking at the peak area for the isolated compound in the gas chromatography—mass spectra analysis of the crude reaction product mixture. It is important to note that in the prior art, yield is often calculated on the basis of the basis of first isolated crude product before final purification. In some embodiments of the process, as discussed below, yield is at least 50%. In other embodiments, the yield is at least 60%. In other embodiments, yield is at least 70%. In yet other embodiments, yield is 70-85%.

Purity is also determined by GC-MS and also by analytical HPLC. The total ion chromatogram from the GC-MS gives information similar to that provided by an FID-GC in that the peak area is proportional to the mass of the analytes detected. Total peak area and the peak areas of the individual analytes can be compared in the GC-MS case as long as the masses are in generally the same range. As discussed below, in some embodiments, purity of the tetrahydrocannabinols isolated by the process is greater than 90%. In yet other embodiments, purity is greater than 95%. In yet other embodiments, purity is greater than 97%. In yet other embodiments, purity is 98-99%.

The invention will now be described by means of examples, although the invention is not limited to these examples.

EXAMPLE I

Conversion of CBD to $\Delta^8$-THC

CBD (300 mg) was added to dried p-toluenesulfonic acid (30 mg) in toluene (15 ml), under $N_2$ atmosphere. In this example, the mixture was refluxed (under $N_2$) for 1 hour, although other time periods may also be used, as discussed below. It was then diluted with ether (20 ml) and poured into cold water, The upper layer was separated, washed with aqueous 5% $NaHCO_3$, then with water, dried over $MgSO_4$ and evaporated. The viscous oil showed mainly one spot on TLC (using 20% ether in petroleum ether as eluent). HPLC, on the crude oil, showed the presence of 86% $\Delta^8$-THC. The oil was chromatographed on a silica gel column (6 g). Elution with 5 to 10% ether in petroleum ether gave a fraction (244 mg, 81%) of $\Delta^8$-THC 98.6% pure. When the reaction was carried out using various reflux times showed the presence of 79.33% $\Delta^8$-THC (15 minutes), 81.7% $\Delta^8$-THC (30 minutes) and 84.6% $\Delta^8$-THC (2 hours).

In the example described above, normal phase HPLC separation is used wherein the column is for example a silica gel and the mobile phase is organic, for example, hexane or ethyl ether-hexane. In other embodiments, reverse phase HPLC separation is used, wherein the column is for example C18 bonded silica gel and the mobile phase is water-methanol or water-acetonitrile. In each case, solvent programming is used.

The p-toluenesulfonic acid is used as a catalyst in the above example. It is of note that boron trifluoride could also be used as a catalyst, as could a number of other Lewis acids known in the art. It is of note that the exact proportion is not essential to the reaction proceeding. It is of further note that the nitrogen atmosphere does not appear as necessary as during the conversion of CBD to $\Delta^9$-THC. It is also of note that other solvents may also be used, for example, benzene, but toluene has produced the best results so far.

In other embodiments, anhydrous $Na_2SO_4$ or another suitable drying or dehydration agent known in the art is used in place of the $MgSO_4$.

In other embodiments, an alkali metal hydrogen carbonate or carbonate of an alkali metal is used instead of $NaHCO_3$.

The nitrogen atmosphere may prevent oxidation of the reaction intermediate, thereby enhancing the yield. Diluting into ether first and then adding the water again prevents undue exposure to oxidizing conditions. The water still quenches the reaction catalyst, but the reaction product is dissolved in the toluene and ether and is to some extent protected. That is, it is not in as intimate contact with the water and not as susceptible to oxidation as it would be if the water were to be added first.

EXAMPLE II

Conversion of CBD to $\Delta^9$-THC $BF_3Et_2O$ (50 µl) was added, under nitrogen atmosphere, to ice cold solution of CBD (300 mg) in dry methylene chloride (15 ml). The solution was stirred at 0° C. for 1 hour. Saturated aqueous solution of $NaHCO_3$ (2 ml) was added until the red color faded. The organic layer was removed, washed with water, dried over $MgSO_4$ and evaporated. The composition of the oil obtained (determined by HPLC): trans-$\Delta^8$-isoTHC 27%, $\Delta^9$-THC 66.7%. The oil was chromatographed on silica gel column (20 g) and eluted with petroleum ether followed by graded mixtures, up to 2:98 of ether in petroleum ether. The first fraction eluted was the $\Delta^8$-iso THC (30 mg, 9.5%) followed by a mixture of $\Delta^8$-iso THC and $\Delta^9$-THC (100 mg). The last compound to be eluted was the $\Delta^9$-THC (172 mg, 57%). The purity of $\Delta^9$-THC (as determined by HPLC) was 98.7%.

It is of note that when the reaction was carried in the presence of $MgSO_4$ (120 mg), the composition of the oil obtained (determined by FIPLC) was: trans-$\Delta^8$isoTHC 20.15%, $\Delta^9$-THC 56.7%.

In the example described above, normal phase HPLC separation is used wherein the column is for example a silica gel and the mobile phase is organic, for example, hexane or ethyl ether-hexane. In other embodiments, reverse phase HPLC separation is used, wherein the column is for example C18 bonded silica gel and the mobile phase is water-methanol or water-acetonitrile. In each case, solvent programming is used.

In other embodiments, anhydrous $Na_2SO_4$ or another suitable drying or dehydration agent known in the art is used in place of the $MgSO_4$.

In other embodiments, another alkali metal hydrogen carbonate or carbonate of an alkali metal is used instead of $NaHCO_3$.

In other embodiments, $BF_3Et_2O$ is dissolved in ethyl acetate, ethanol, hexane or other suitable organic solvent.

In other embodiments, the catalyst is hydrochloric acid in ethanol or sulfuric acid in cyclohexane (reaction mixture refluxed rather than stirred).

While the preferred embodiments of the invention have been described above, it will be recognized and understood that various modifications may be made therein, and the appended claims are intended to cover all such modifications which may fall within the spirit and scope of the invention.

The invention claimed is:

1. A method of converting cannabidiol (CBD) to $\Delta^9$-tetrahydrocannabinol ($\Delta^9$-THC) comprising:
   providing a reaction mixture comprising CBD in dry methylene chloride;
   adding $BF_3Et_2O$ to the reaction mixture;
   stirring the ice cold reaction mixture under a nitrogen atmosphere;
   adding $NaHCO_3$ to the reaction mixture;
   allowing the mixture to separate into an aqueous phase and an organic phase;
   removing the organic phase;
   washing the organic layer with water; and
   eluting $\Delta^9$-THC from the organic phase, purity of the eluted $\Delta^9$-THC being greater than 97%.

2. The method according to claim 1 including stirring the reaction mixture for approximately 1 hour.

3. The method according to claim 1 including drying the organic phase over $MgSO_4$ and evaporating the organic phase following washing.

4. The method according to claim 1 including eluting the organic phase on an HPLC column.

5. The method according to claim 4 wherein the $\Delta^9$-THC is eluted with ether in petroleum ether following washing the column with petroleum ether.

6. The method according to claim 5 wherein the ether in petroleum ether is 2 parts ether in 98 parts petroleum ether.

7. The method according to claim 1 including eluting the organic phase on an RP-HPLC column.

* * * * *